US011406313B2

(12) United States Patent
Moorman et al.

(10) Patent No.: US 11,406,313 B2
(45) Date of Patent: Aug. 9, 2022

(54) SYSTEM AND METHOD FOR IMPROVED CARDIAC RHYTHM CLASSIFICATION FROM THE TIME BETWEEN HEART BEAT INTERVALS USING NON-LINEAR DYNAMICS

(71) Applicant: UNIVERSITY OF VIRGINIA PATENT FOUNDATION, Charlottesville, VA (US)

(72) Inventors: J. Randall Moorman, Keswick, VA (US); Douglas E. Lake, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 508 days.

(21) Appl. No.: 15/319,240

(22) PCT Filed: Jun. 17, 2015

(86) PCT No.: PCT/US2015/036238
§ 371 (c)(1),
(2) Date: Dec. 15, 2016

(87) PCT Pub. No.: WO2015/195806
PCT Pub. Date: Dec. 23, 2015

(65) Prior Publication Data
US 2017/0127964 A1 May 11, 2017

Related U.S. Application Data

(60) Provisional application No. 62/013,112, filed on Jun. 17, 2014.

(51) Int. Cl.
| | |
|---|---|
| *G01N 33/48* | (2006.01) |
| *G06F 15/00* | (2006.01) |
| *A61B 5/361* | (2021.01) |
| *A61B 5/00* | (2006.01) |
| *G06K 9/00* | (2022.01) |
| *A61B 5/316* | (2021.01) |
| *G16Z 99/00* | (2019.01) |
| *G16H 50/30* | (2018.01) |
| *G16H 50/20* | (2018.01) |
| *G16H 50/70* | (2018.01) |

(52) U.S. Cl.
CPC .............. *A61B 5/361* (2021.01); *A61B 5/316* (2021.01); *A61B 5/7264* (2013.01); *G06K 9/00563* (2013.01); *G16H 50/20* (2018.01); *G16H 50/30* (2018.01); *G16Z 99/00* (2019.02); *G16H 50/70* (2018.01)

(58) Field of Classification Search
None
See application file for complete search history.

(56) References Cited

U.S. PATENT DOCUMENTS

| | | | |
|---|---|---|---|
| 2007/0073177 A1 | 3/2007 | Kontothanassis et al. | |
| 2007/0208263 A1 | 9/2007 | John et al. | |
| 2009/0012412 A1 | 1/2009 | Wiesel | |
| 2010/0056940 A1 | 3/2010 | Moorman et al. | |
| 2013/0030481 A1 | 1/2013 | Ghosh et al. | |
| 2014/0244644 A1* | 8/2014 | Mashinchi ............ | G06F 16/284 707/737 |

OTHER PUBLICATIONS

Winship et al. Regression Models With Ordinal Variables (American Sociological Review, vol. 49 (1984) pp. 512-525).*
Friedman, Jerome H., Forest Baskett, and Leonard J. Shustek. "An algorithm for finding nearest neighbors." IEEE Transactions on computers 100.10 (1975): 1000-1006.*
Mishra, Amit K., and Shantanu Raghav. "Local fractal dimension based ECG arrhythmia classification." Biomedical Signal Processing and Control 5.2 (2010): 114-123.*
Extended European Search Report dated Jan. 22, 2018, issued by the European Patent Office in corresponding European Application No. EP 15808970.6 (9 pages).
International Search Report (PCT/ISA/210) dated Sep. 16, 2015, by the United States Trademark Patent Office as the International Searching Authority for International Application No. PCT/US2015/036238.
Written Opinion (PCT/ISA/237) dated Sep. 16, 2015, by the United States Trademark Patent Office Patent Office as the International Searching Authority for International Application No. PCT/US2015/036238.
Office Action (Communication) dated Mar. 6, 2019, by the European Patent Office in corresponding European Patent Application No. 15808970.6. (7 pages).
Office Action (Summons to Attend Oral Proceedings) dated Feb. 12, 2021, by the European Patent Office in corresponding European Patent Application No. 15808970.6. (9 pages).

(Continued)

*Primary Examiner* — Anna Skibinsky
(74) *Attorney, Agent, or Firm* — Buchanan Ingersoll & Rooney PC

(57) ABSTRACT

A system for classifying cardiac rhythms is disclosed. The system includes one or more processors, one or more computer-readable tangible storage devices, and program instructions stored on at least one of the one or more storage devices for execution by at least one of the one or more processors. The program instructions include first program instructions to obtain data representative of a time series of the times between heartbeats. The program instructions further comprise second program instructions to segment the time series into a plurality of segments. The program instructions further comprise third program instructions to calculate a plurality of parameters corresponding to each of the 30-second segments. The program instructions further comprise fourth program instructions to analyze the obtained data and the calculated parameters using a plurality of multivariable algorithms for rhythm classification. The program instructions further comprise fifth program instructions to synthesize the results of the plurality of multivariable algorithms to formulate a single rhythm classification.

3 Claims, 12 Drawing Sheets

(56) References Cited

OTHER PUBLICATIONS

Office Action (Result of Consultation) dated Sep. 9, 2021, by the European Patent Office in corresponding European Patent Application No. 15808970.6. (18 pages).

* cited by examiner

SYSTEM AND METHOD FOR IMPROVED CARDIAC RHYTHM CLASSIFICATION FROM THE TIME BETWEEN HEART BEAT INTERVALS USING NON-LINEAR DYNAMICS

CROSS-REFERENCE TO RELATED APPLICATIONS

This application claims priority from U.S. Provisional Patent Application No. 62/013,112 filed on Jun. 17, 2014, which is incorporated by reference herein in its entirety.

BACKGROUND

Several common clinical scenarios call for identification of cardiac rhythm in ambulatory out-patients. For example, atrial fibrillation ("AF") is a common arrhythmia that is often paroxysmal in nature. Decisions about its therapy are best informed by knowledge of the frequency, duration and severity of the arrhythmia. For patients with AF, clinicians must make complex decisions about oral anticoagulation, rate control with drugs or cardiac ablation with pacemaker therapy, and rhythm control with drugs or ablation procedures. The implications for anticoagulation therapy alone are enormously important, as the rate of stroke goes up sharply with even short episodes of AF. These therapies have been shown to lower the risk of clinical thromboembolism in all patients with AF, regardless the different types as paroxysmal, persistent or permanent. However, in the lowest-risk patients, the bleeding risk associated with anticoagulant therapy can exceed the risk of thromboembolism without therapy, thus, decision-making regarding the initiation of antithrombotic treatments requires an accurate estimation of both embolic and bleeding risk.

While implanted devices can record information about duration, frequency and severity of AF with great accuracy, non-invasive diagnostic devices for recording electrocardiographic signals are constrained by the need for skin electrodes. Current solutions for cardiac rhythm detection is limited to high fidelity monitoring that can only be used for short periods, or low-fidelity monitoring for longer periods. They require ECG leads and a digital recording device. While much smaller than in years past, such a recording apparatus may still be obtrusive. Even the high fidelity monitoring can be limited by noisy and distorted waveform data. The most frequently available and reliably accurate data set is the time series of the times between heartbeats or pulses, also referred to as RR interval time series. However, non-invasive devices for determining heart rhythm are not in common use because of reduced confidence in detecting AF based on the heart rate or RR series alone. Specifically, sinus rhythm (SR) with frequent ectopy is expected to share many time series features with AF, and thus be difficult to distinguish. In addition, other transient cardiac arrhythmias cause short-lived symptoms but are difficult to diagnose without skin electrode-based recording devices.

PVCs, alone, lead to poorer prognosis, even in patients with no obvious heart disease. Further evidence lies in the fact that the ejection fraction rises in the great majority of patients with very frequent PVCs and low ejection fraction at the time of PVC ablation.

In ambulatory outpatients, where continuous monitoring currently requires specialized equipment and services, the finding of atrial fibrillation has profound implications for cardiac testing and for therapies. For patients with atrial fibrillation, clinicians must make complex decisions about oral anticoagulation, rate control with drugs or cardiac ablation with pacemaker therapy, and rhythm control with drugs or ablation procedures. The implications for anticoagulation therapy alone are enormously important, as the rate of stroke goes up sharply with even short episodes of atrial fibrillation. The new diagnosis of atrial fibrillation in patients who are monitored because of stroke of unknown origin can lead to life-saving therapy.

In hospital in-patients, the new onset of paroxysmal atrial fibrillation is often interpreted as a sign of clinical deterioration arising from unbalanced activity of the sympathetic and parasympathetic arms of the autonomic nervous system. In addition to the standard decisions about anticoagulation, rate control and rhythm control just noted, clinicians must consider possible causes of deterioration such as sepsis, other infection, hemorrhage, incipient cardiac or respiratory therapy. As a result of the new arrhythmia diagnosis, they may re-examine the patient and order new tests or therapies. New-onset atrial fibrillation in an otherwise apparently stable patient might lead to new decisions about transfers to intensive care units, or decisions about prolonging the hospital stay.

In intensive care unit ("ICU") patients, where very close monitoring is essential to detect even slight changes for the worse, EKG monitoring is nearly always present. ICU patients can be very unstable, and major changes in diagnosis and therapy can come swiftly. Accurate detection of cardiac rhythm changes in real time can make the difference between life and death.

In the operating room, surgeons and anesthesiologists must make decisions about the status of the patient very quickly indeed. Here, new-onset atrial fibrillation may lead directly to cardioversion, and atrial and ventricular ectopy are very likely to be treated with antiarrhythmic drugs to prevent sustained arrhythmia.

In the Emergency Department, the stability of patients and the severity of their injuries and illness must be accurately assessed at top speed. Cardiac arrhythmias are important clues to guide not only initial therapies, but also differential diagnoses.

Thus detection and quantification of atrial fibrillation, atrial ectopy and ventricular ectopy is an important clinical mandate throughout the spectrum of clinical care.

For ambulatory outpatients, the current art for detection is limited to high-fidelity monitoring that can only be used for short periods, or low-fidelity monitoring for longer periods. The current art requires EKG leads, and a digital recording device. While much smaller than in years past such recording apparatus is obtrusive. Even the high-fidelity monitoring can be limited by noisy and distorted waveform data.

Some hospital in-patients are not continuously monitored by EKG telemetry. Instead, observations are limited to hourly visits by nurses and other health care personnel. Moreover, an increasing number of atrial or ventricular ectopic beats can be an early warning of sustained atrial or ventricular arrhythmia. Intermittent observation alone may mean that these important findings are missed altogether.

Although ICU and operating room patients are continuously monitored, it is the value of the heart rate that is of first concern, and important changes in rhythm such as the appearance of atrial fibrillation or increasing ectopic burden may go undetected.

The most frequently available and reliably accurate data set is the time series of the times between heartbeats. This is derived from ventricular activation leading to the high amplitude QRS complex of the EKG, which is usually discernible even when noise obscures the much smaller P wave that represents atrial activation and is essential in detecting sinus rhythm from all others. This can be referred to as the RR interval time series. Time series measures that can distinguish among sinus rhythm, atrial fibrillation and ectopy of atrial or ventricular origin can be of great use in clinical care.

While algorithms have been developed that distinguish between normal sinus rhythm and atrial fibrillation, there has been no effective solution to distinguish either of these rhythms from the condition of sinus rhythm and degrees of frequency of atrial and ventricular ectopy. Specifically, sinus rhythm with very frequent ectopy is not distinguishable from atrial fibrillation using available algorithms.

RR interval time series measures that can distinguish among normal sinus rhythm, AF and ectopy of atrial or ventricular origin (PACs and PVCs) can be of great use in clinical care. One approach to rhythm classification using only RR interval time series is to examine their dynamics. We can expect, for example, that NSR has a regular and repeating characteristic, that AF is irregular, and that SR with ectopy has a regular baseline with intermittent departures. Numerous algorithms to analyze RR interval time series for clinical purposes exist. These are usually classified as time domain, frequency domain, phase domain, non-linear dynamical domain, although new classifications of statistical, geometric, energetic, informational and invariant domains have been suggested. Known methods have been shown to have modest effect in distinguishing patients at high or low risk, or degrees of illness severity for patients in SR with little or no ectopy. Some have been effective in distinguishing AF from other rhythms, principally SR with little or no ectopy. Examples include coefficient of sample entropy, a histographic method, and a Poincare plot-based method. However, known methods do not distinguish AF from the condition of SR and degrees of frequency of atrial and ventricular ectopy. Specifically, known methods do not distinguish SR with very frequent ectopy from AF.

For example, the entropy of RR interval time series has been studied as a means for detecting AF in short RR interval time series. The results show very clear distinction between AF and NSR that is free of ectopy, but there is an area of overlap where entropy measures are the same for AF compared to SR with frequent ectopy. It may be desirable to characterize the RR interval time series that can elucidate the cardiac rhythm when the entropy measurement is ambiguous.

SUMMARY

A system for classifying cardiac rhythms is disclosed. The system includes one or more processors, one or more computer-readable tangible storage devices, and program instructions stored on at least one of the one or more storage devices for execution by at least one of the one or more processors. The program instructions include first program instructions to obtain data representative of a time series of the times between heartbeats. The program instructions further comprise second program instructions to segment the time series into a plurality of segments. The program instructions further comprise third program instructions to calculate a plurality of parameters corresponding to each of the 30-second segments. The program instructions further comprise fourth program instructions to analyze the obtained data and the calculated parameters using a plurality of multivariable algorithms for rhythm classification. The program instructions further comprise fifth program instructions to synthesize the results of the plurality of multivariable algorithms to formulate a single rhythm classification.

A computer program product for classifying cardiac rhythms is disclosed. The computer program product includes one or more computer-readable tangible storage devices, and program instructions stored on at least one of the one or more storage devices. The program instructions include first program instructions to obtain data representative of a time series of the times between heartbeats. The program instructions further comprise second program instructions to segment the time series into a plurality of segments. The program instructions further comprise third program instructions to calculate a plurality of parameters corresponding to each of the 30-second segments. The program instructions further comprise fourth program instructions to analyze the obtained data and the calculated parameters using a plurality of multivariable algorithms for rhythm classification. The program instructions further comprise fifth program instructions to synthesize the results of the plurality of multivariable algorithms to formulate a single rhythm classification.

BRIEF DESCRIPTION OF THE DRAWINGS

In the accompanying drawings, structures are illustrated that, together with the detailed description provided below, describe exemplary embodiments of the claimed invention. Like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration.

DETAILED DESCRIPTION

Figure 1:
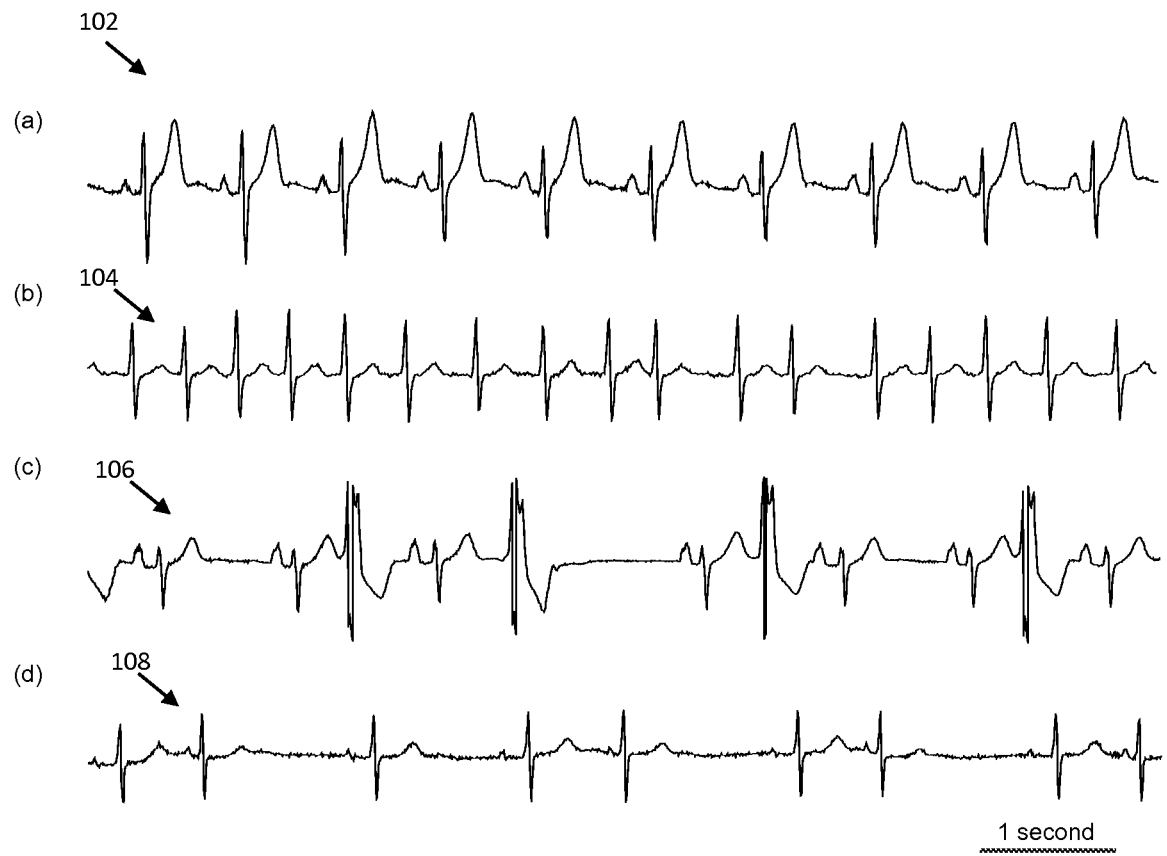
FIG. 1 illustrates example ECGs of four patients.

An aspect of an embodiment of the present disclosure provides a new approach, method, computer readable medium, and system in which the entropy measurement is used in conjunction with other time series measurements in the time and non-linear dynamical domains. The insight is that higher dimensional characterizations of the time series properties successfully separate the classes of rhythm. The example that is developed relies on three dynamical measures, such as entropy, local dynamics and correlations. The coefficient of sample entropy ("COSEn") is efficient at detecting AF from NSR, but yields intermediate values for SR with ectopy. The local dynamics score ("LDs") detects the combination of reduced heart rate variability ("HRV") with ectopy, and is a powerful predictor of 2 year mortality in ambulatory patients undergoing Holter monitoring. Finally, the familiar detrended fluctuation analysis ("DFA") informs on long range correlations and has been studied in aging, heart failure, and in predicting AF after coronary bypass surgery.

An aspect of an embodiment of the present disclosure provides an overall approach, method, computer readable medium, and system that calculate time series measures in both the time domain, including moments (in particular the first two, the mean and variance), and the non-linear dynamical domain. Other kinds of time series measures might also be calculated such as those in frequency domain, phase domain, or other.

The results are combined using any of the many available multivariable classification schemes, including multivariable logistic regression, k nearest neighbor, neural nets, Bayesian nets, CART analysis, random forests, decision trees, and others.

The mechanisms for each method's ability to add information about the classification problem can be understood. For example, the utility of mean heart rate in the scheme is that atrial fibrillation is often faster than sinus rhythm. The entropy of atrial fibrillation time series is higher than sinus rhythm.

The detrended fluctuation analysis is useful to detect atrial and ventricular ectopy. The calculation is of the root mean square of the res.

The detrended fluctuation representation of local residuals as a function of window size shows little change for windows of length 4 to 12 because the ectopic beats force the local fit of the trend to a value that is not equal to the mean. The resulting residuals are relatively large, but their values do not depend on the window length.

While there have been other time series measures approaches to cardiac rhythm classification, this approach differs in its independence from waveform analysis, relying only on RR interval time series, its inclusion of multiple measures from various mathematical domains, and its use of probabilistic approaches for synthesis of multiple variables.

It should be appreciated that classification models can be developed for specific clinical settings. Models are likely to differ between, for example, outpatients undergoing ambulatory cardiac monitoring for suspicion of transient arrhythmia and patients in an ICU. In the latter, it is highly likely that there are baseline differences in, for example, the first two moments, the mean heart rate and the heart rate variability.

It should be further appreciated that other and non-cardiac clinical factors may mandate different rhythm classification models. For example, atrial fibrillation is very rate before age 30, but is very common indeed after age 80.

Practice of an aspect of an embodiment (or embodiments) of the disclosure will be still more fully understood from the following examples and experimental results, which are presented herein for illustration only and should not be construed as limiting the disclosure in any way.

In one example, a RR interval time series that is 10 minutes in duration is obtained. This duration is selected for the example because changes over 10 minutes are clinically suitable for assessment of changes in patient status. The RR interval time series is then segmented into 30-second sections. This length of time is selected for this example because this is the minimum duration of an episode of atrial fibrillation that is clinically noteworthy. The traditional and novel parameters on each 30-second segment is then calculated and the 10-minute epoch is characterized by its mean, median, percentile or quartile of the up to 20 results.

Next, using training and test sets of RR interval time series for which the rhythm diagnosis was made using traditional means, such as interpretation by a clinician, multivariable algorithms for rhythm classification are developed and validated. Such algorithms include logistic, ordinal or other regression, nearest neighbor analysis, neural or Bayesian networks, data mining, CART or other decision trees, rough set theory, and other past, present and future multivariable statistical pattern recognition and classification strategies.

The results of multiple classification schemes are then combined. For example, one might distinguish among 3 rhythm classes by creating 3 pairwise logistic regression models that employ time series metrics as inputs. For any new data set, these result in multiple probability estimates of the candidate rhythms. These can be synthesized by the using the highest single estimate from any of the models as the final classification, or using other means for multivariable analysis.

It should be appreciated that other data analytical techniques can be applied to the sequential outputs of the modeling strategy. For example, once a rhythm diagnosis has been decided, hysteresis may be applied so that a higher than usual level of evidence is required to change to another classification.

Materials and Methods

Study population: RR interval time series were studied from 24 hour Holter recordings collected from 2722 consecutive patients at the University of Virginia Heart Station from December 2004 to October 2010. The age of the patients varied from 0 to 100 years, with an average value of 47±25 years. Atrial fibrillation ("AF"), premature atrial contraction ("PAC") and premature ventricular contraction ("PVC") labels were obtained from an automatic classifier. The RR series were subdivided into 377,285 10-minute segments. Each 10-minute segment was classified as AF if the burden of AF was greater than 5%, as sinus rhythm ("SR") with ectopy if the burden of PAC or PVC was more than 10%, as normal sinus rhythm ("NSR") otherwise. Thus, the dataset is composed of 79% NSR, 8% AF and 13% SR with ectopy segments. The 3 categories are mutually exclusive and reflect clinical practice Heart rate metrics: Means and standard deviations were computed for 30-second segments and averaged results for each 10-minute segment. To investigate the HR dynamics, the Coefficient of Sample Entropy ("COSEn"), Detrended Fluctuation Analysis ("DFA") and the Local Dynamics score ("LDs") were computed.

Coefficient of Sample Entropy ("COSEn"): COSEn is an entropy measure derived from the Sample Entropy ("SampEn") and designed specifically to detect AF in very short RR interval time series. Generally, entropy estimators measure the degree of regularity of a signal by counting how many template patterns repeat themselves. Repeated patterns imply order and lead to low values of entropy. In particular, sample entropy is the negative natural logarithm of the conditional probability that two sequences of length m that match within tolerance r will also match at the m+1st point. Defining as A the total number of matches of length m+1 and B the total number of matches of length m, then the conditional probability (cp) is equal to A/B. The sample entropy is computed as:

$$SampEn = -\ln(cp) = -\ln(A/B) = -\ln(A) + \ln(B) \quad (1)$$

If A and B are equal, which means that the time series is very regular, the entropy measure is zero, whereas if A is smaller than B, this leads to a higher value of entropy.

The choice of the parameters m and r is crucial in order to obtain a reliable estimation of the conditional probability, especially in very short time series. It has been proposed to convert the measured conditional probability to a probability density. The new measure was named Quadratic Sample Entropy ("QSE") and it consists of normalizing the sample entropy by the volume of each matching region, $2r^m$. The equation (1) becomes:

$$QSE = -\ln\left(\frac{A}{(2r)^{m+1}}\right) - \left(-\ln\left(\frac{B}{(2r)^m}\right)\right) \quad (2)$$
$$= -\ln(cp) + \ln(2r)$$
$$= SampEn + \ln(2r)$$

QSE allows direct comparison of results obtained by using different values of r. Regression analyses has shown that heart rate was an important independent predictor of AF. Hence, the COSEn measure requires the subtraction of the natural logarithm of the mean RR interval:

$$COSEn = SampEn + \ln(2r) - \ln(\text{mean } RR \text{ interval}) \quad (3)$$

The choice of r and m reflects the standards and findings already described. Therefore m=1 and r=30 msec is chosen. COSEn was calculated over 30-second segments, consistent with the clinical idea that AF must usually last 30 sec to be considered.

Detrended fluctuation analysis: DFA has been proposed as a way to quantify the fractal-like scaling properties of RR interval time series. The interbeat intervals time series of total length N is first integrated:

$$y(k) = \sum_{i=1}^{k} [B(i) - B_{ave}] \quad (4)$$

where B(i) is the ith interbeat interval and $B_{ave}$ is the average interbeat interval. Next, the integrated time series is divided into non overlapping boxes of equal length, n. In each box a least-squares line is fitted to represent the trend in that box. Let $y_n(k)$ be the y coordinate of the straight line segments. The integrated time series, y(k), is detrended by subtracting the local trend $y_n(k)$ in each box. The root-mean-square fluctuation of this integrated and detrended time series is:

$$F(n) = \sqrt{\frac{1}{N} \sum_{k=1}^{N} [y(k) - y_n(k)]^2} \quad (5)$$

This computation is repeated over all the box sizes. The results from each box length are averaged—fewer points contribute to the plotted value for higher n. Typically, F(n) will increase with the box size n. A linear relationship on a log-log plot of F(n) versus the box size n indicates the presence of power law (fractal) scaling. Under such conditions, the fluctuations can be characterized by a scaling exponent. In particular, if the data are long-range correlated, F(n) increases as a power-law with respect to n, $F(n) \sim n^\alpha$. Thus, the fluctuation scaling exponent can be determined by a linear fit on the log-log plot. For uncorrelated data, such as white noise, the scaling exponent is $\alpha=0.5$. A slope larger than 0.5 indicates persistent long-range correlations. In contrast, $0<\alpha<0.5$ indicates an anti-persistent type of correlation. The slope equal to 1 is the theoretical value which corresponds to 1/f noise, and $\alpha=1.5$ to Brownian noise. The original calculation of the DFA was proposed for long signals, such as 24 hr Holter ECG recordings, but it was used also in shorter interval time series. Thus, the scaling exponent a was calculated on the 10-minute segments over the box size range of 4 to 12.

Local Dynamics Score (LDs): The LDs is an index to investigate the local dynamics of short RR series. In particular, how often individual templates in a short series match each other is examined. Given a 12-beat segment, the algorithm consists mainly into counting the number of times each sample matches with the other 11 with a tolerance r of 20 msec. A histogram of the count of templates as a function of the number of matches is constructed. If no points match, a bar of 12 counts appears in the bin 0, and all the other bins are empty, when all 12 points match each other, the histogram will have a bar of 12 counts in bin 11.

The LDs is computed as a linear combination of the values in bin 0, bin 10 and bin 11; the coefficients are normalized so as to sum to 1. A uniform distribution of matches, i.e. the counts in all bins, equal to 1 leads to LD score of 1. Lower scores imply a bell-shape histogram distribution and higher scores imply a distribution concentrated on either or both extremes of the histogram.

In one example, the score is calculated for every 10-minute segment from the average of the 12-beat histograms.

Statistical Analysis: In one example, Kruskal-Wallis ANOVA was used to compare the index values among the three groups (NSR, AF, SR with ectopy) and post-hoc multiple comparisons were performed by the Wilcoxon rank-sum test using the Bonferroni correction. For this univariate statistical analysis, only a single 10-minute segment for each patient was randomly selected. To test the overall hypothesis that dynamical measures are useful for rhythm classification, several schemes were used. In particular, the accuracy of classification was compared using means and SD alone, and after addition of the dynamical measures COSEn, LDs and DFA. The first scheme was a system of 3 multivariate logistic regression models, each used to distinguish one rhythm class from the other two. The final classification of the RR series was obtained by using the highest probability estimate among the three models. The second approach was a k-nearest neighbors technique. All models were validated using a 10-fold cross-validation procedure on the entire dataset.

Results

An example of analysis: FIG. 1 illustrates ECGs of four patients from the UVa Holter database. Four different rhythms are illustrated: NSR 102, AF 104, SR with PVCs 106 and SR with PACs 108.

Figure 2:
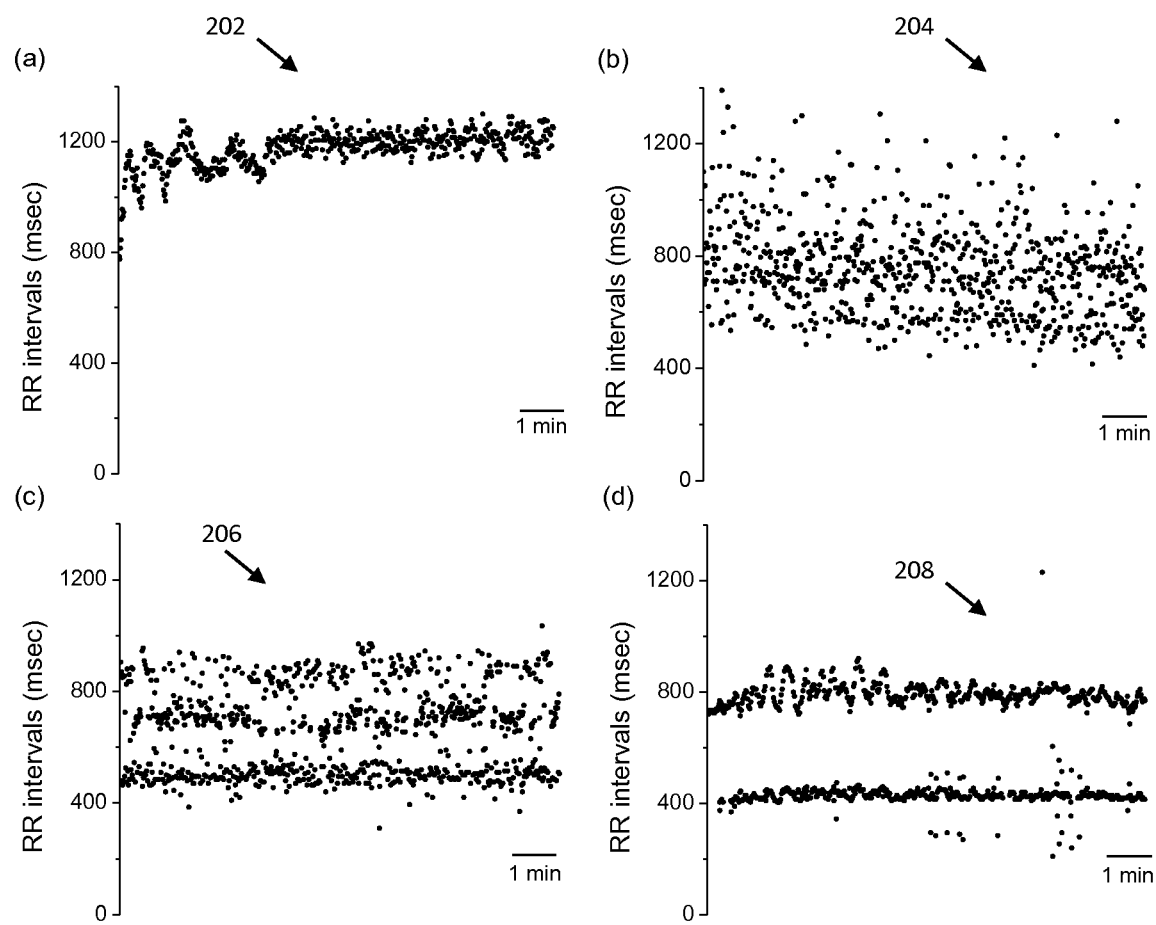
FIG. 2 illustrates example 10 minute segments of the RR interval time series from the same ECG recordings displayed in FIG. 1.

FIG. 2 illustrates 10 minute segments of the RR interval time series from the same ECG recordings displayed in FIG. 1. In this example, it was considered that a 10-minute record of SR with a high burden of PVCs 206 is equal to 57% and a very high burden of PACs 208 is equal to 73%.

Figure 3:
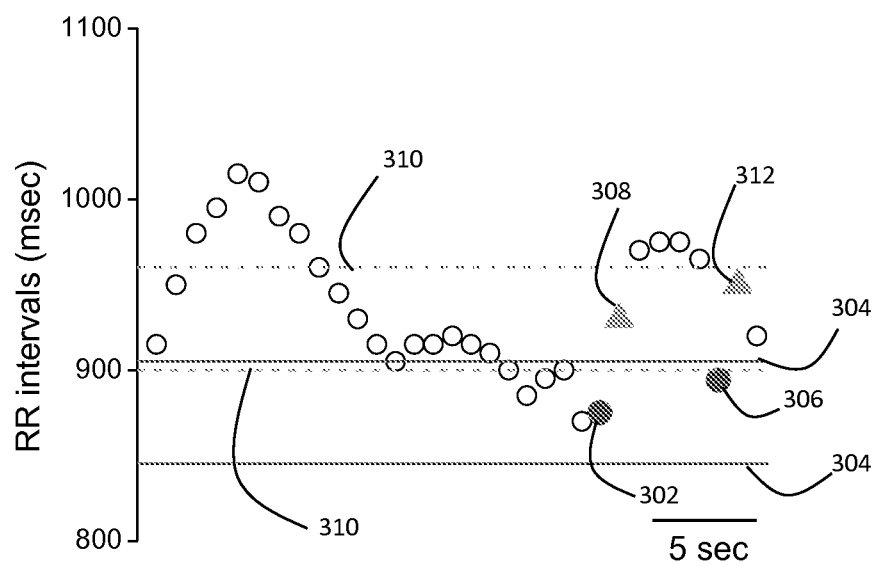
FIG. 3 illustrates an example of the procedure of counting matches over the first 30 seconds extracted from the RR series of FIG. 2.

FIG. 3 illustrates an example of the procedure of counting matches, which is the core of the COSEn estimation, over the first 30 seconds extracted from the RR series 202 of FIG. 2. For a template of length m=1 (depicted as dot 302) and a tolerance r=30 msec (depicted as solid lines 304), the number of matches is obtained by counting all subsequent points that fall within r, that is, within the tolerance range marked by the solid lines 304. In this case only one match occurs at the second dot 306. Next, all the matches for a template of length m+1 (first dot 302 and first triangle 308) are counted. The dashed lines 310 delimits now the tolerance interval for the triangles 308 and 312. A match occurs when all the points of the template are within a distance r of any other m+1 segment in the signal. Thus, in this case, there is only one match. Finally, the natural logarithm of the ratio between the total number of matches of length m+1 and length m is divided by the factor 2r, and subtracted by the natural logarithm of the mean of RR intervals. COSEn is so obtained.

The series 204 illustrated in FIG. 2 is associated with the highest value of COSEn=−0.48, as the AF epoch is the most irregular signal, while an intermediate value characterizes SR with PVCs (COSEn=−1.29, 206 illustrated in FIG. 2, where the high burden of ventricular ectopy increases the low values usually associated to NSR epoch. In fact COSEn=−2.11 in NSR epoch 202 and a low value of COSEn=−1.82 was obtained also for SR with PACs 208. This results is expected for NSR, since the characteristic of this type of signal is its regularity, while in the case of SR with PACs it can be explained by the fact that high burdens of ectopic beats such bigeminy, can lead to a very regular patterns.

Figure 4:
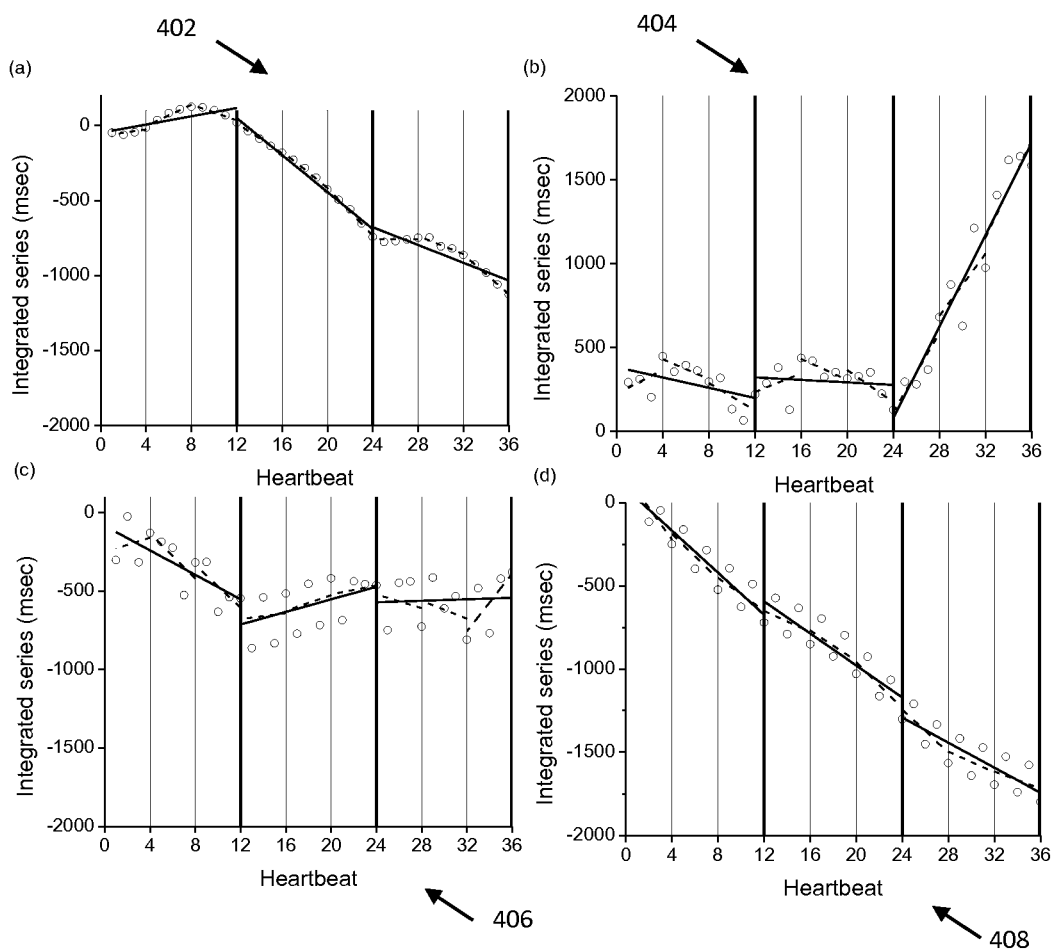
FIG. 4 illustrates an example of detrending procedure for the DFA, corresponding to the trends illustrated in FIG. 2.

FIG. 4 illustrates an example of detrending procedure 402-408 for the DFA, corresponding to the trends 202-208 illustrated in FIG. 2. In this example, only the first 36 RR interval time series of each trend 202-208 in FIG. 2 are shown and the detrending procedure is illustrated for box size n=4 and n=12. Note that the variations from the solid lines are large, especially in 402 and 404.

Figure 5:
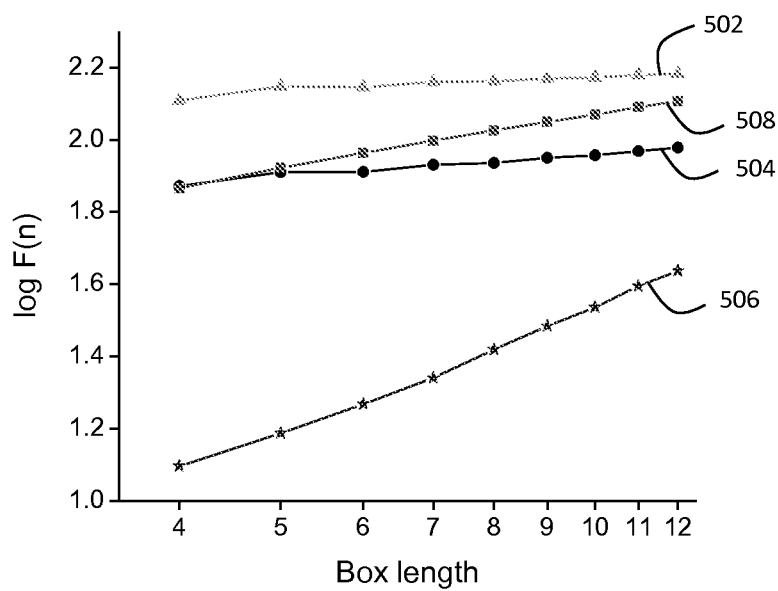
FIG. 5 illustrates the results for the 4 RR interval time series illustrated in FIG. 2.

FIG. 5 illustrates the results for the 4 RR interval time series 202-208 illustrated in FIG. 2. The 10-minute epochs classified as SR with PVCs 502 (line with triangles) and SR with PACs 504 (line with circles) have a flat trend with a slope equal to 0.18 and 0.3, respectively, the epoch classified as NSR 506 (line with stars) shows the trend with the highest slope, equal to 1.11. Finally, the trend classified as AF 508 (line with squares) lays in the intermediate region with a value of slope equal to 0.46 which is close to the theoretical value of 0.5 related to uncorrelated signals.

To explain these results, referring again to FIG. 4: with black circles is represented the integrated time series, the dashed red and solid green lines indicates the linear interpolation for box size n=4 and n=12, respectively. Looking at the distance between the circles and the dashed red line, it is clear how F (n) for box length equal to 4 differs among the groups: NSR (a) has the lowest value, AF (b), SR with PACs (d) and PVCs (c) have increasing higher values. As the scale n becomes bigger, a mutual increase of F (n) is appreciable in all the 4 groups—looking at the distance between the circles and the solid green lines, but with very different scales. For NSR the increment is elevated, and this is reflected by the highest value of the slope, for AF it is still significant but lower than NSR, and the slope, consequently, has a reduced value. In the cases of SR with ectopic beats the increase is very little, generating almost flat lines in the log-log plot; the scaling exponents are the lowest.

LDs is computed on the averaged histogram of template count as a function of template matches calculated every 12 beats.

Figure 6:
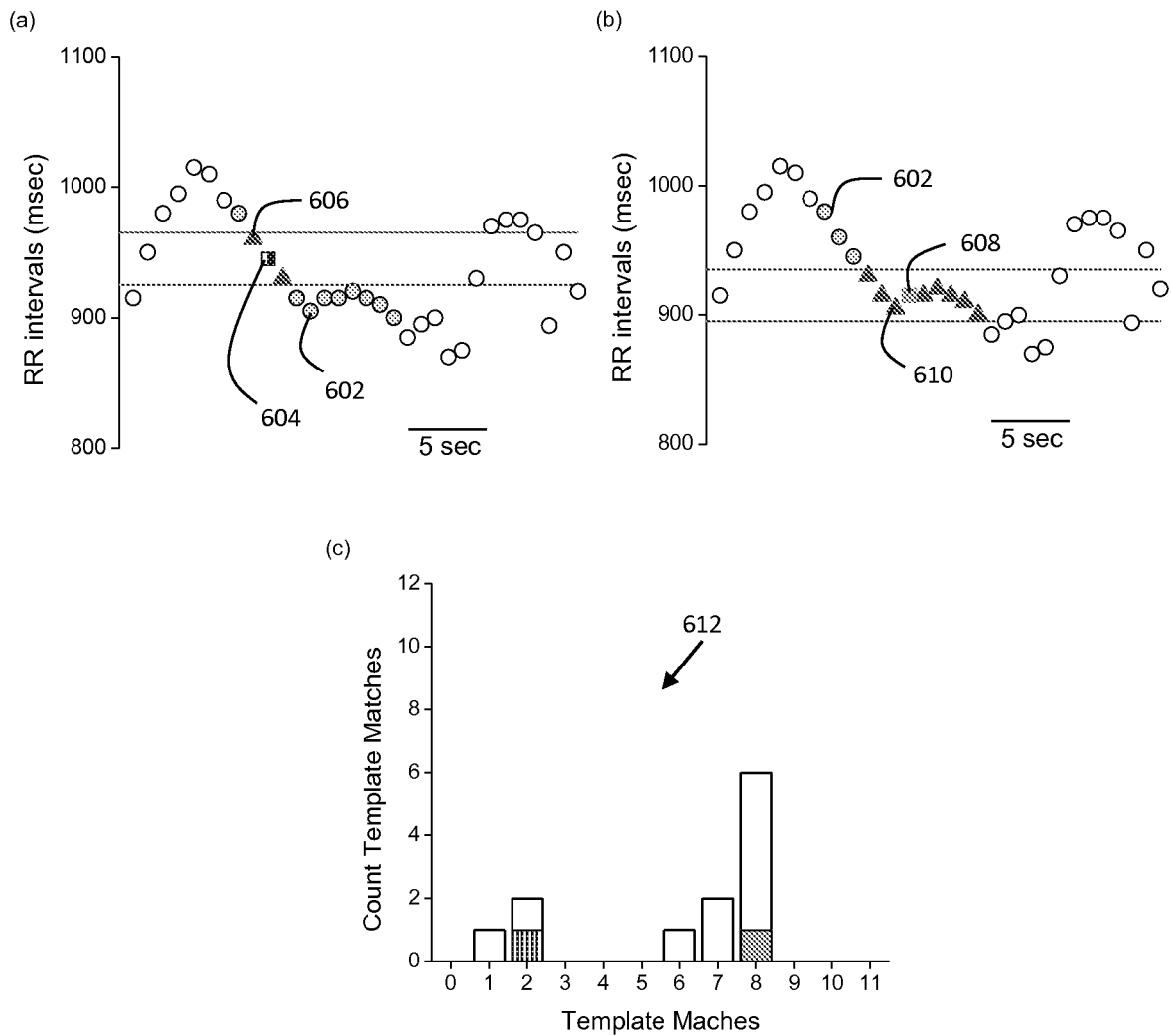
FIG. 6 illustrates the step-by-step procedure in a 12-beat segment extracted from the same 30-second record of FIG. 3.

FIG. 6 illustrates the step-by-step procedure in a 12-beat segment 602 extracted from the same 30-second record of FIG. 3. Two points are considered: the half square 604 has 2 matches 606, whereas the full square 608 counts 8 matches 610 within a tolerance of 20 msec. The contribution of each of the two interbeat intervals to the histogram is highlighted in 612. Repeating this counting for all the 12 points, the final histogram of the templates counts as a function of the number of matches is obtained.

Figure 7:
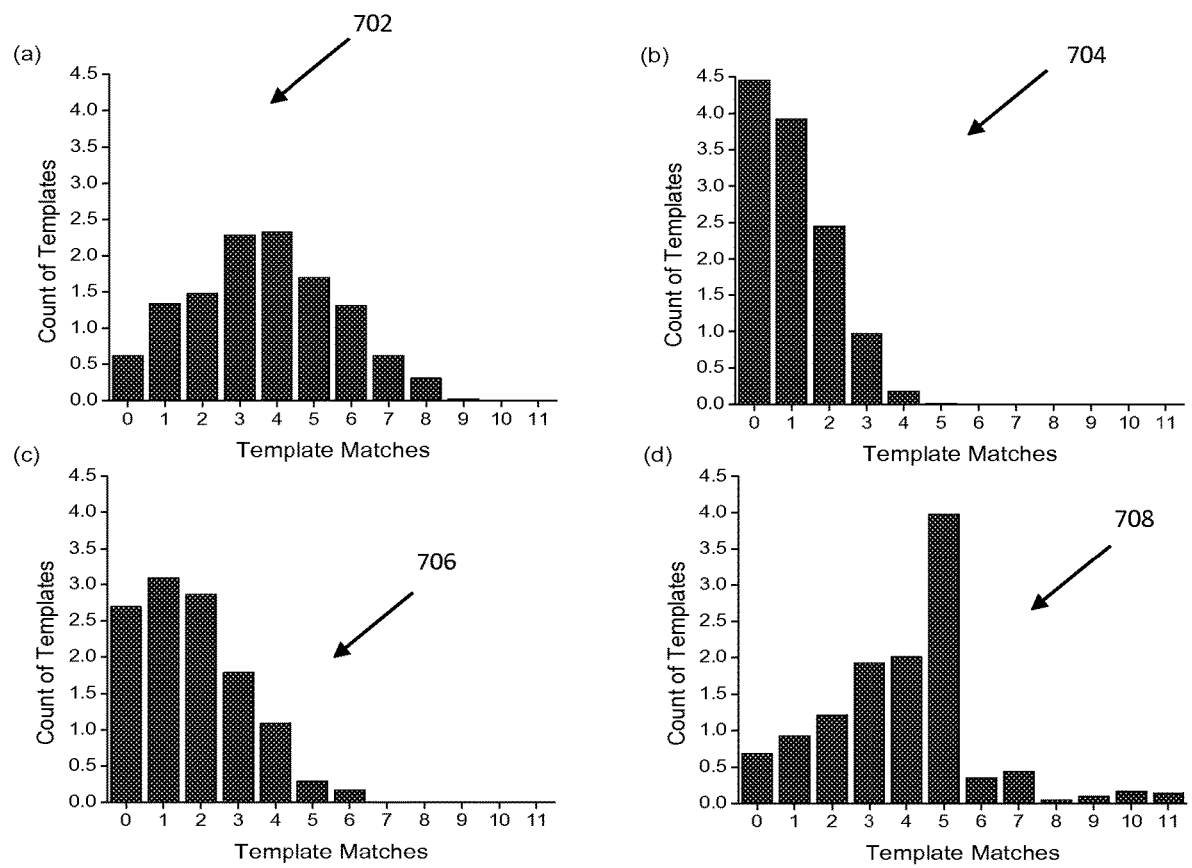
FIG. 7 illustrates the average histograms for the 10-minute segments represented in FIG. 2.

The average histograms for the 10-minute segments represented in FIG. 2 are illustrated in FIG. 7. As expected, in AF condition most templates find very few matches 704, whereas a bell-shape histogram distribution was obtained for the NSR series 702. In case of PVCs the histogram is similar to the AF case, due to the high amount of ventricular ectopic beats which produces high values in the first bins of the histogram 706. For SR with PACs 708, the histogram reports a peak in correspondence of bin 5 and the majority of templates finds a number of matches less than 5. Intuitively, the peak appears due to the alternation of accelerated and delayed beats, associated to the bigeminy.

LDs is computed on the histograms. The highest score of 2.05 belongs to AF, as expected, followed by SR with PVCs (LDs=1.24), due to its high burden of ectopy. NSR and SR with PACs both have a low score, equal to 0.28 and 0.54, respectively. This is expected in the case of NSR, due to its distribution mainly concentrated in the center of the histogram, while in the case of SR with PACs the low value is related to the specific pattern of bigeminy, which corresponds to low counts in bins 0, 10 and 11.

Figure 8:
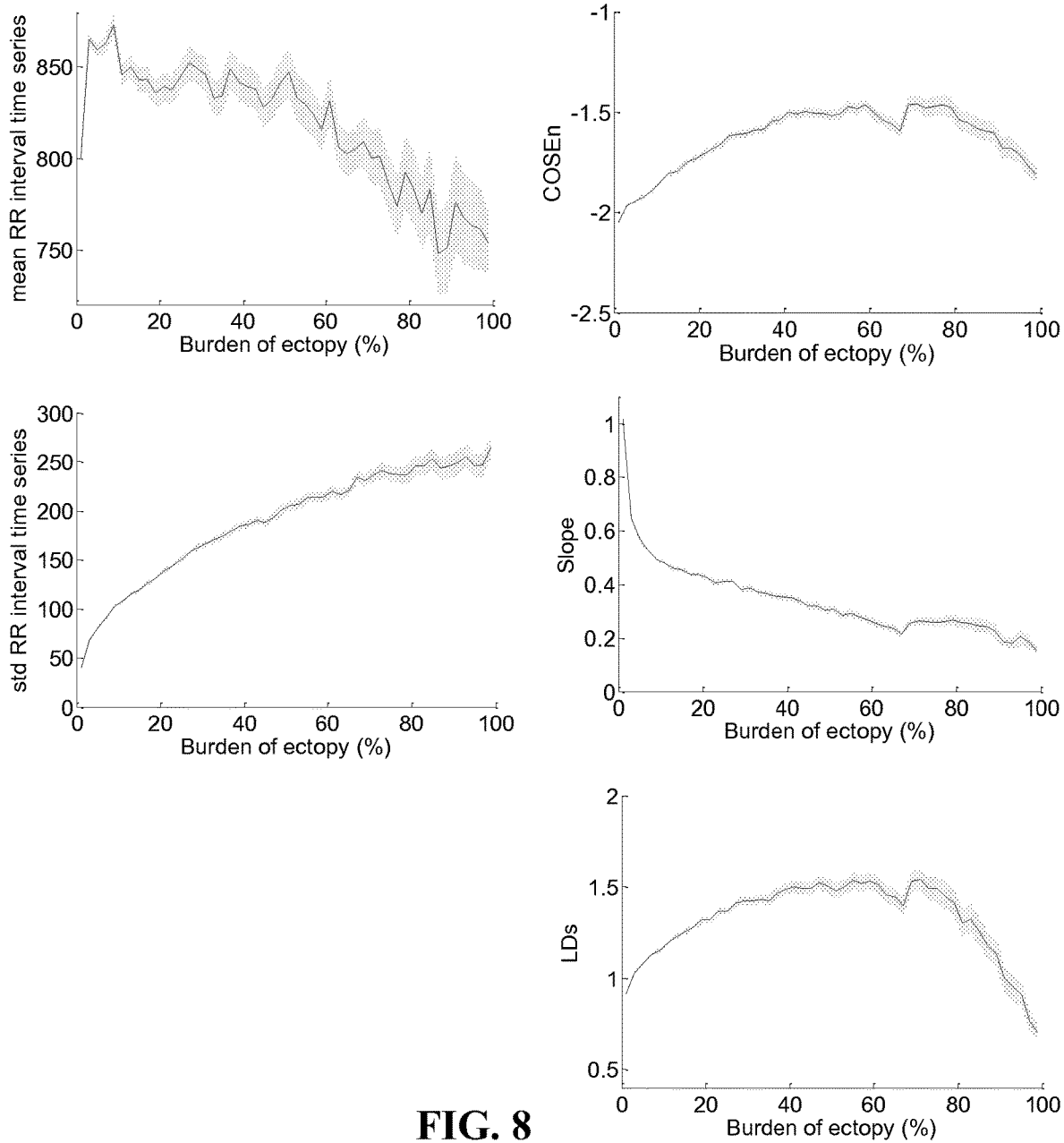
FIG. 8 illustrates the distribution of each index as a function of the burden of ectopy calculated on all 10-minute records.

Effect of ectopy on dynamical measures: FIG. 8 illustrates the distribution of each index as a function of the burden of ectopy calculated on all 10-minute records, with the 95% confidence interval. Each bin in the figure represents the mean and CI computed every 2% after ranking according to ectopy burden.

As expected, ectopic beats increase entropy and the related LDs—after a point—though, entropy falls with increased ectopy. This may be caused by the particular arrhythmias named trigeminal and bigeminal rhythms, or non-sustained atrial and ventricular tachycardia. The regularity of these abnormal rhythms accounts for the lower entropy values.

The fall in DFA slope reflects the effects of ectopic beats on the dynamics of the RR interval time series. The physiological condition ("NSR") is characterized by long-range correlations, the presence of ectopic beats plays a role such as an uncorrelated noise. As a resulting effect, the slope values falls below 0.5.

Univariate analysis: Table I shows the mean values for each group and for each parameter. Significant differences were obtained for all the parameters except for mean and the standard deviations of RR interval time series. As expected, NSR had the lowest variability, entropy and LDs, and the highest DFA.

TABLE I

Median and IQR values of the parameters for each group

| Parameters | AF | NSR | SR with ectopy | Kruskal-Wallis test p-value |
|---|---|---|---|---|
| Mean RR (sec) | 763.3 ± 224.6[b] | 795.1 ± 253.2[b] | 819.6 ± 235.8 | <0.001 |
| Std RR (sec$^2$) | 149.2 ± 70.7 | 37.67 ± 33.18[a,b] | 152 ± 99.4 | <0.001 |

TABLE I-continued

Median and IQR values of the parameters for each group

| Parameters | AF | NSR | SR with ectopy | Kruskal-Wallis test p-value |
|---|---|---|---|---|
| COSEn | −0.504 ± 0.491[b] | −2.08 ± 0.434[a,b] | −1.694 ± 0.567 | <0.001 |
| LDs | 1.924 ± 0.861[b] | 0.836 ± 0.807[a,b] | 1.285 ± 0.61 | <0.001 |
| DFA | 0.61 ± 0.1[b] | 0.98 ± 0.59[a,b] | 0.32 ± 0.28 | <0.001 |
| Age | 71.9 ± 13.9[b] | 47 ± 43.1[a,b] | 58.4 ± 53.5 | <0.001 |

Post-hoc comparisons p-value < 0.05:
[a] vs AF,
[b] vs SR with ectopy

Logistic regression analysis: The strategy of classification is based on three multivariate logistic regression models, each used to discriminate one group from the other two. This parametric analysis hypothesized a linear relationship among the effects of the independent predictor variables on the predicted output.

Table II shows the accuracy of labeling 10-minute records using the standard factors model. The columns give the correct classification based on the labels provided by the software. The rows show the classification results from the model adopted. The accuracy is 88.3% and the positive predictive accuracy values are 62.4%, 93.7% and 62.7%, respectively for AF, NSR and SR with ectopy.

TABLE II

Contingency matrix of Multi-label model with linear measures

| | AF | NSR | SR with ectopy |
|---|---|---|---|
| AF | 32.44% | 0.28% | 9.49% |
| NSR | 12.96% | 98.92% | 31.19% |
| SR with ectopy | 54.6% | 0.8% | 59.32% |

Table III shows the accuracy of labeling 10-minute records considering the second model, when also non-linear indices are taken into account. The accuracy of the classification rises to 94.1% and the positive predictive accuracies becomes 89.1%, 95.8% and 85.5%.

TABLE III

Contingency matrix of Multi-label model with dynamical measures

| | AF | NSR | SR with ectopy |
|---|---|---|---|
| AF | 80.35% | 0.26% | 4.21% |
| NSR | 10.31% | 98.44% | 18.87% |
| SR with ectopy | 9.33% | 1.3% | 76.93% |

A fixed threshold to classify a segment as NSR or SR with ectopy was chosen equal to 10%, reflecting clinical practice. However, one of the most common errors of this system are situations of SR with little amount of ectopy, which are the main causes of misleading with NSR. We further tested the accuracy of the new model by varying the threshold from 4% to 20% with an increasing step of 2%. An improvement of the exact match of segments classified as SR with ectopy was obtained from a value of 55.5% (4% burden) to 89.7% (20% burden), while NSR accuracy decreases of about 4%. The overall accuracy rose from 88.9% to 93.7% and peaked at 94.4% in correspondence of a threshold of 14% burden.

K-nearest neighbor analysis: A 10-minute segment was classified based on the classification of the majority of neighbors considered. For a new test record $x_i$, distances from all the points of the training set are sorted in ascending order. Depending on the number of neighbors K, the first K smallest distances are chosen and their classes are taken into account for the final decision: the new record is assigned a probability to be in one of the three classes and the higher value was selected for the classification. This analysis requires no model, because it belongs to the nonparametric clustering methods category. For the K-NN analysis a first selection of the optimal parameters was necessary, in particular, the metric for calculating the distance between the current query point and the training set, and the number of neighbors (K). We analyzed three distance metrics: the Euclidean distance, the standardized Euclidean distance and the Mahalanobis distance. Their efficiency was tested on the same dataset using a 10-fold cross-validation procedure with an initial value of K=1. The overall accuracy of the classification in the three cases was 87.9%, 92.8% and 92.7%, respectively. The standardized Euclidean distance was selected for further investigations.

Figure 9:
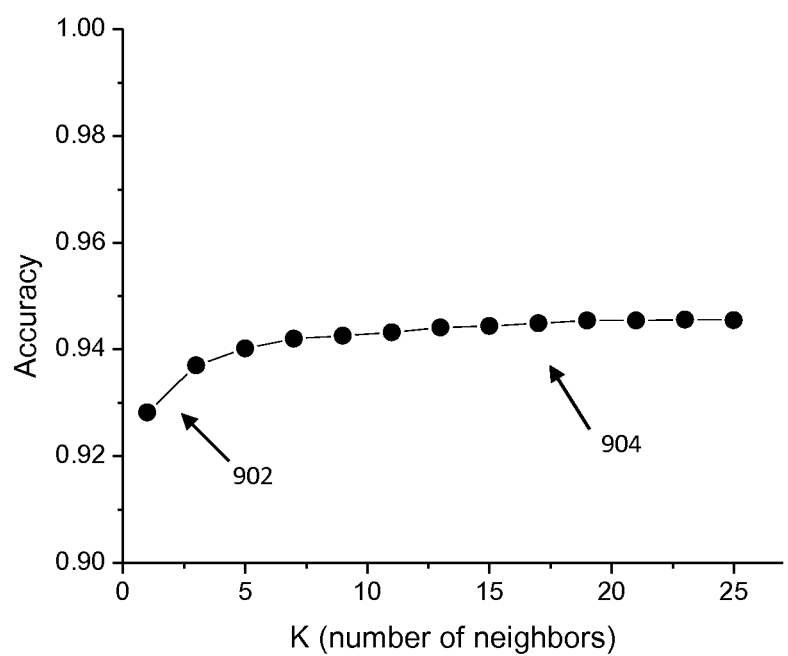
FIG. 9 illustrates the accuracy of the classifier with the chosen distance metrics as a function of the number of neighbors K.

FIG. 9 illustrates the accuracy of the classifier with the chosen distance metrics as a function of the number of neighbors K. It rises for small K 902, but for values greater than 15 a plateau is reached 904, near a value of 94.55%. We chose K=25 for this analysis.

Tables IV and V report the accuracy obtained with the K-NN classifier of labeling 10-minute records using the standard factors model and the new model, respectively. The total accuracy is 89.4% in the first case and equal to 94.55% in the second case. Positive predictive accuracies are 89.7%, 96.7% and 84% respectively for AF, NSR and SR with ectopy.

TABLE IV

Contingency matrix of k-NN model with linear measures

| | AF | NSR | SR with ectopy |
|---|---|---|---|
| AF | 72.80% | 0.34% | 15.67% |
| NSR | 7.54% | 97.96% | 16.40% |
| SR with ectopy | 19.66% | 1.7% | 67.93% |

TABLE V

Contingency matrix of k-NN model with dynamical measures

| | AF | NSR | SR with ectopy |
|---|---|---|---|
| AF | 81.31% | 0.38% | 4.48% |
| NSR | 8.89% | 97.76% | 14.01% |
| SR with ectopy | 9.8% | 1.86% | 81.51% |

Figure 10:
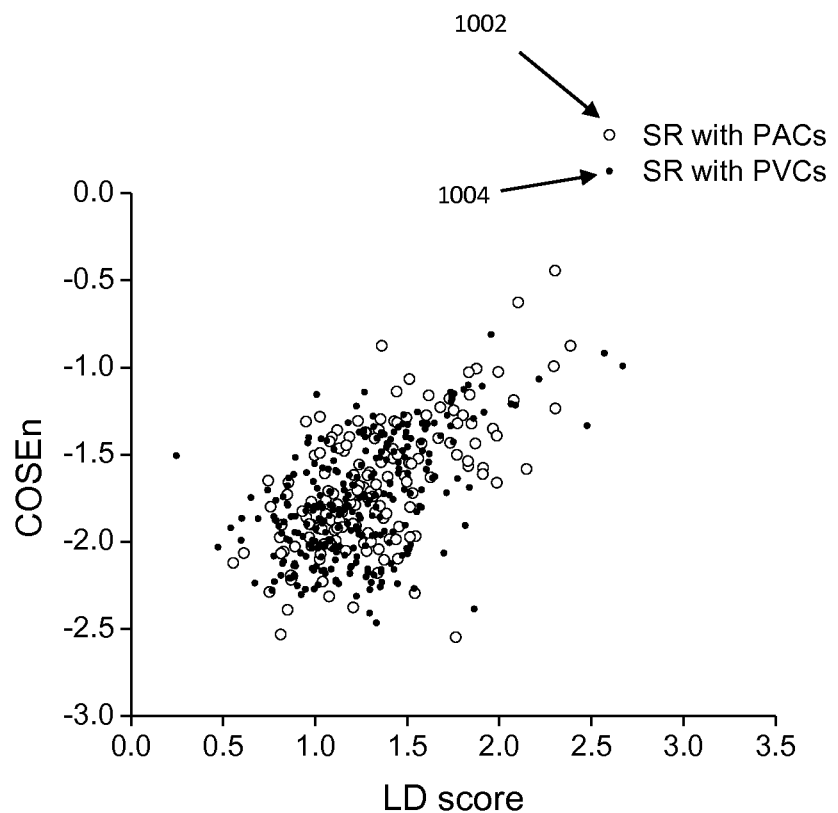
FIG. 10 illustrates the distribution of COSEn and LDs for the UVa Holter population calculated as an average over 24 hours.

Individual considerations of premature atrial and ventricular contractions: FIG. 10 illustrates the distribution of COSEn and LDs for the UVa Holter population calculated as an average over 24 hours. SR with PVCs 1004 or PACs 1002 are highlighted with dots and circles, respectively. Interestingly, we do not find large differences in the dynamics of atrial and ventricular ectopy, visible in the great overlap between the two classes. This is clinically counter-intuitive, as the coupling intervals of PVCs 1004 are perceived to be regular than those of PACs 1002. We can find, though, no direct comparisons of the dynamics of atrial and ventricular ectopy reported to shed light on this issue. We confirmed this result testing a new strategy of classification with 4 logistic regression models for a further discrimination between SR with PVCs 1004 or PACs 1002. The final decision classified the RR series by using the highest output among the four models. Table VI shows the results. An accurate differentiation of the two situations of ectopy is not feasible: low accuracies are associated with the two classes of ectopy, with a big misclassification of SR with PVCs 1004 as SR with PACs 1002 (42.96%) and high percentages of misleading with NSR. Moreover, the value of 13.02% of error between SR with PACs and AF model shows that the two arrhythmias are easily confused, a situation that can be reasonably expected. Positive predicted accuracies are equal to 84.6%, 94.4%, 64.7% and 57.6%, for AF, NSR, SR with PVCs and PACs, respectively. When considering the two classes of ectopy together in a three-based models scheme, the positive predicted accuracy rises to 85.5%. These findings led us to choose a classification strategy based on three models.

TABLE VI

Contingency matrix of Multi-label model with 4 groups

|  | AF | NSR | SR with PVCs | SR with PACs |
|---|---|---|---|---|
| AF | 0.8296 | 0.0029 | 0.0313 | 0.1302 |
| NSR | 0.1209 | 0.9904 | 0.2546 | 0.3073 |
| SR with PVCs | 0.0312 | 0.0057 | 0.6790 | 0.4296 |
| SR with PACs | 0.0184 | 0.0010 | 0.0351 | 0.1329 |

Figure 11:
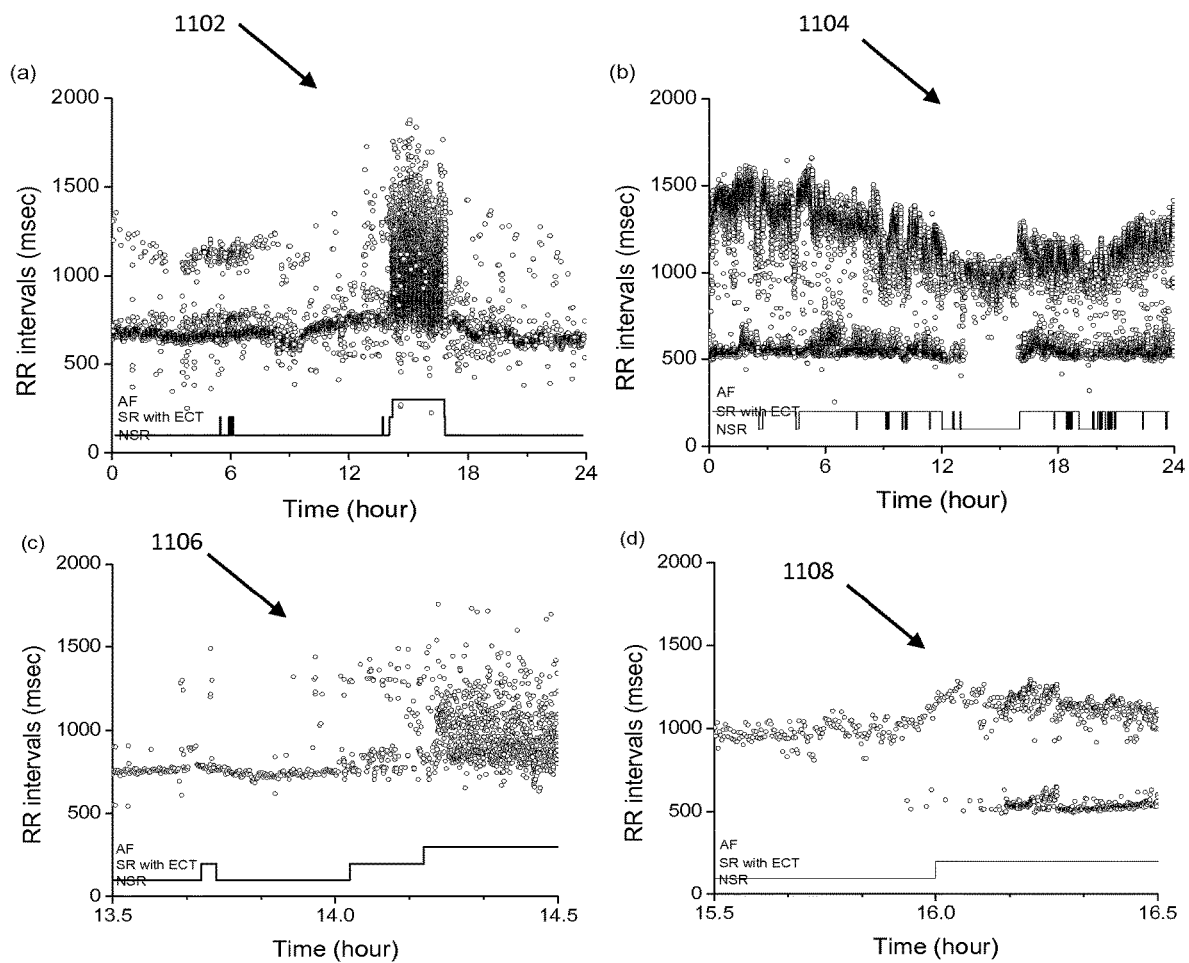
FIG. 11 illustrates two examples of continuous monitoring with a 24-hour Holter recording, where an update of the model output is performed every two minutes.

Real-time behavior of the classifier: The effectiveness of the classifier in a real-time context was tested, where changes in few minutes could be important. FIG. 11 illustrates two examples of continuous monitoring with a 24-hour Holter recording, where an update of the model output is performed every two minutes. As the figure illustrate, the proposed model can track sudden changes in heart rhythm. In the upper panels 1102 and 1104 there are two examples of 24-hour recordings from two distinct patients of the UVa Holter database. In 1102, an AF episode occurs after about 14 hours and sparsely episodes of ectopic beats are present; in 1104, the rhythm is dominated by atrial premature contractions, unless a 4-hour periods of NSR. The lower solid line indicates the output of the classifier proposed in this work with an update every 2 minutes. In the bottom panels a zoom of the previous signals is presented: in 1106, the transition from NSR to AF, preceded by episodes of atrial ectopies; in 1108, the transition from NSR to SR with PACs.

Validation in the MIT-BIH database: The MIT-BIH AF Database consists of 10-hour recordings from 25 patients with AF with 1.22M RR intervals, 42.5% labeled as AF. The ARH Database consists of 30-minute recordings from 48 patients with various arrhythmias with 0.1M RR intervals, 11% labeled as AF. The NSR Database consists of 24-hour recordings from 72 patients with a total of 7.52M RR intervals, some of them labeled as ectopy but none labeled as AF. In all, there are 11,196 10-minute segments in the combined data sets, 644 that we labeled as AF. This 6% prevalence of AF is similar to the 10% in the UVa Holter data set. In contrast, though, is the small number of 10-minute segments with 10% or more ectopic beats—only 94.

For external validation purposes, the regression-based scheme and the k-NN algorithm was tested on the individual and combined MIT-BIH data sets divided into 10-minute segments. Tables VII a-d and VIII a-d show the results of the rhythm classifications achieved by the regression-based schemes and k-NN respectively.

TABLE VII a

LR on MIT-BIH AF database

|  | AF | NOAF |
|---|---|---|
| AF | 485 (77%) | 8 (1%) |
| NSR | 92 (15%) | 718 (85%) |
| SR with ectopy | 49 (8%) | 118 (14%) |

TABLE VII b

LR on MIT- BIH ARH database

|  | AF | NSR | SR with ectopy |
|---|---|---|---|
| AF | 14 (78%) | 0 (0%) | 5 (17%) |
| NSR | 3 (17%) | 56 (97%) | 3 (10%) |
| SR with ectopy | 1 (6%) | 2 (3%) | 21 (72%) |

TABLE VII c

LR on MIT- BIH NSR database

|  | AF | NSR | SR with ectopy |
|---|---|---|---|
| AF | 0 | 8 (0%) | 1 (2%) |
| NSR | 0 | 9631 (100%) | 7 (11%) |
| SR with ectopy | 0 | 40 (0%) | 57 (71%) |

TABLE VII d

LR on all 3 combined MIT database

|  | AF | NSR | SR with ectopy |
|---|---|---|---|
| AF | 499 (77%) | 16 (%) | 6 (6%) |
| NSR | 95 (15%) | 10400 (100%) | 10 (11%) |
| SR with ectopy | 50 (8%) | (%) | (%) |

TABLE VIII a kNN on MIT- BIH AF database

|  | AF | NOAF |
|---|---|---|
| AF | 565 (77%) | 39 (5%) |
| NSR | 61 (15%) | 776 (95%) |
| SR with ectopy | 0 (0%) | 0 (0%) |

TABLE VIII b kNN on MIT- BIH ARH database

|  | AF | NSR | SR with ectopy |
|---|---|---|---|
| AF | 0 (0%) | 0 (0%) | 3 (10%) |
| NSR | 2 (33%) | 58 (100%) | 7 (24%) |
| SR with ectopy | 10 (56%) | 0 (0%) | 19 (66%) |

TABLE VIII c kNN on MIT-BIH NSR database

|  | AF | NSR | SR with ectopy |
|---|---|---|---|
| AF | 0 | 0 (0%) | 0 (0%) |
| NSR | 0 | 9679 (100%) | 61 (94%) |
| SR with ectopy | 0 | 0 (0%) | 4 (6%) |

TABLE VIII d kNN on all 3 combined MIT database without age

|  | AF | NSR | SR with ectopy |
|---|---|---|---|
| AF | 564 (88%) | 20 (0%) | 30 (32%) |
| NSR | 78 (12%) | 10529 (100%) | 56 (60%) |
| SR with ectopy | 2 (0%) | 3 (0%) | 8 (9%) |

Discussion and Conclusion

The problem of arrhythmia detection and classification based on RR series were studied using linear and dynamical measures to discriminate among NSR, AF and SR with ectopy. In 2722 24-hour ambulatory EKG recordings from patients divided into 10-minute RR series, entropy was measured using coefficient of sample entropy, scaling exponent using detrended fluctuation analysis, and local dynamics using a new local dynamics score. The hypothesis that these measures added to standard measures of HR and HRV using model-based and model-free statistical classifiers was tested. The major finding is improved distinction of SR with ectopy using the dynamical measures. The positive predictive accuracy using either regression models or kNN analysis was 85%, with higher values for the diagnosis of NSR (96%) and AF (90%). The threshold to classify a segment as SR with ectopy, as opposed to NSR, was only a 10% burden—this reflects clinical practice, and accuracy increased further if the threshold for diagnosing ectopy was higher.

The models were internally validated using 10-fold cross-validation and externally validated in the canonical MIT-BIH databases of NSR, AF and other arrhythmias (ARH). There, the positive predictive accuracies for NSR and AF rose to 99% and 96%, respectively, but fell for SR with ectopy to 46%. This may be explained by the much lower incidence of SR with ectopy in the highly selected MIT-BIH databases, where they represented <1% of the 11,196 10-minute segments, compared with 13% of the 377,825 10-minute segments in the UVa database from consecutive patients.

These measures do not distinguish well between atrial and ventricular premature beats, a potentially important clinical distinction. Atrial premature beats may be harbingers of AF, and ventricular premature beats are associated with increased mortality, especially when structural heart disease is present.

Clinical aspects of rhythm classification: Clinical emphasis constrains analysis in several ways. First, atrial flutter was considered to be the same as AF. This approach, which is based on the similarities in clinical management, is certain to lead to misclassifications. The dynamics of atrial flutter when AV conduction is fixed can never be considered the same as AF: The regularity with which AFL rhythm can appear is responsible for most of the 7 to 10% misclassification error of AF as NSR. Second, the diagnosis of AF was assigned when as little as 30 seconds, or 5% of a 10-minute segment was present. This is consistent with clinical practice, where episodes lasting this long elicit full consideration in authoritative guidelines, count toward AF burden, and thus can lead to full AF treatment measures. Finally, the diagnosis of ectopy was assigned when as little as 10% is present, as noted above. The end result of these classification decisions leads us to diagnoses of AF and SR with ectopy even when the rhythm is 90% or more purely normal SR.

Clinical implications: The clinical importance of accurate detection of AF is related to the specific treatments that the presence of the arrhythmia requires. For example, the distinction between AF and SR with ectopy can be difficult without PQRST waveforms, but is nonetheless important for two reasons. First, the diagnosis of AF calls for decisions about anticoagulation, rate control and rhythm control. Second, atrial ectopy may presage AF, and ventricular ectopy may lead to cardiomyopathy or in other ways increase the risk of mortality. An atrial ectopy burden of even less than 1% increases the risk of AF over the next 5 to 15 years. More than 10% ventricular ectopy can be associated with LV dysfunction and clinical heart failure syndromes that are reversed by ablation of the ectopic site.

Applications: The utility of this classification are represented by its ability to work on segments of only 10 minutes, allowing it to be potentially useful in a real time context. For example, continuous monitoring in the Intensive Care Unit can be crucially important since changes in the cardiac rhythm are very abrupt and life-threatening. An example of this application is reported in FIG. 10 where the proposed classifier was proved to be able to track sudden changes in heart rhythm. Home care monitoring and telemedicine is also a broad field where automatic RR-based algorithms for arrhythmias detection could find extensive applications.

Considering Table II and Table III a big decrease in all misclassification errors is relevant, leading to an increase of the overall accuracy from 88.3% to 94.1%. The greatest improvement is related to a reduced misleading between AF and SR with ectopy, while NSR is classified with approximately the same accuracy. Positive predicted accuracy values rise remarkably from about 62% in both cases of AF and SR with ectopy to 89.1% and 85.5%, respectively. NSR positive predicted accuracy rises only of about 2%. Equivalent results are obtained in Table IV and V, when the measures are tested with a non-parametric method.

However, one of the most common errors of this system are situations of SR with little amount of ectopy, which are the main causes of misleading with NSR. By increasing the threshold from a value of 4% to a value of 20% a mutual rise of about 34% of SR with ectopy accuracy is also observed, while NSR accuracy decreases of about 4%.

In this disclosure, three nonlinear measures are propsoed—COSEn, scaling exponent from DFA and LDs—to combine to heart rate and heart rate variability, reaching a discrimination among NSR, AF and SR with PVCs or PACs with an accuracy of more than 94%. Moreover the majority of the other algorithms are tested on the MIT-BIH database which is limited. The researched described in this disclosure was performed on a bigger and real-world dataset composed of 24 hour ECG recordings collected at the University of Virginia Heart Station from 2722 patients.

A limitation in the study described herein is represented by Atrial Flutter, because they can lead to a ventricular rhythm either fixed at a portion of the atrial rate, reaching even 300-400 beats/minute, or can be irregular as AF. PVCs and PACs cannot be distinguished with good accuracy when considering an approach based on 4 models (Table VI). Thus, analysis was limited to a three models-based classification.

A limit for this sort of classification is represented by Atrial Flutter, because the possible occurrences as regular rhythms usually lead to wrong diagnoses. Despite this important limitation, AFL with AF was included in the analysis because the clinical treatments required are the same in both cases, especially with regard to the important issue of anticoagulation. For example, removing the 18 patients with AFL from the analysis the overall accuracy for logistic regression rises to 94.54%, mostly due to a reduction of misclassification error of AF with NSR, which decreases from 10.31% to 7.64%. For K-NN classifier the findings are the same.

The high risk of stroke associated with AF involves specific antithrombotic therapies for the patient, as oral anticoagulants. However, a balanced evaluation of the risk of stroke and the risk of bleeding, linked to the anticoagulation treatment, is needed in the decision-making process, to properly decide when to start the therapy. Usually when the burden of AF is low, say, less than 5%, treatments are not undertaken; in contrast, when the burden is higher the AF episode has a big clinical importance and it is specifically treated. Situations where lots of ectopy are present may lead to a mistake in the diagnosis and this has to be avoided in order to properly decide if the therapy has to be initiated.

However, large differences in the dynamics of atrial and ventricular ectopy were not found. This is clinically counter-intuitive, as the coupling intervals of PVCs are perceived to be regular than those of PACs. However, no direct comparisons of the dynamics of atrial and ventricular ectopy reported can be found to shed light on this issue.

Figure 12:
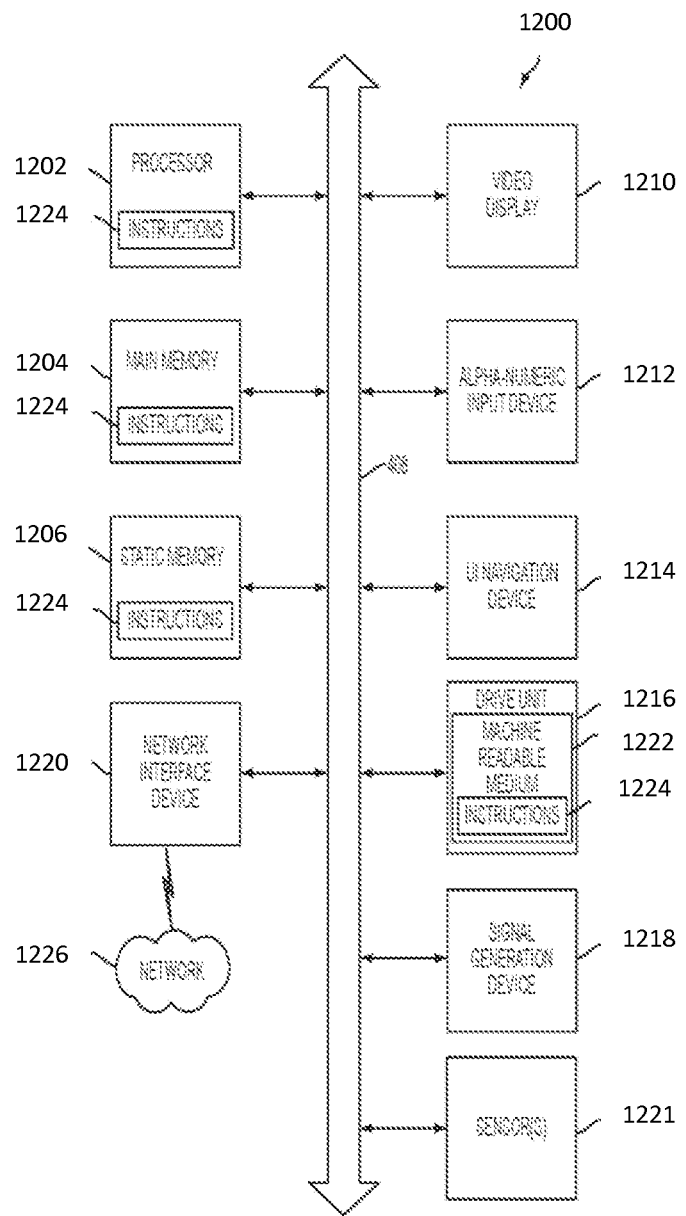
FIG. 12 illustrates a block diagram of an example computing system.

FIG. 12 illustrates a block diagram of an example computing system 1200 that can be used to implement one or more embodiments of the system and method discussed herein.

The computing system 1200 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system 1200 can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware and software architectures that can be deployed in example embodiments.

In an example, the computing system 1200 can operate as a standalone device or the computing system 1200 can be connected (e.g., networked) to other computing systems.

In a networked deployment, the computing system 1200 can operate in the capacity of either a server or a client machine in server-client network environments. In an example, computing system 1200 can act as a peer machine in peer-to-peer (or other distributed) network environments. The computing system 1200 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the computing system 1200. Further, while only a single computing system 1200 is illustrated, the term "computing system" shall also be taken to include any collection of computing systems that individually or jointly execute a set (or multiple sets) of instructions to perform any one or more of the methodologies discussed herein.

Example computing system 1200 can include a processor 1202 (e.g., a central processing unit (CPU), a graphics processing unit (GPU) or both), a main memory 1204 and a static memory 1206, some or all of which can communicate with each other via a bus 1208. The computing system 1200 can further include a display unit 1210, an alphanumeric input device 1212 (e.g., a keyboard), and a user interface (UI) navigation device 1211 (e.g., a mouse). In an example, the display unit 1210, input device 1217 and UI navigation device 1214 can be a touch screen display. The computing system 1200 can additionally include a storage device (e.g., drive unit) 1216, a signal generation device 1218 (e.g., a speaker), a network interface device 1220, and one or more sensors 1221, such as a global positioning system (GPS) sensor, compass, accelerometer, or other sensor.

The storage device 1216 can include a machine readable medium 1222 on which is stored one or more sets of data structures or instructions 1224 (e.g., software) embodying or utilized by any one or more of the methodologies or functions described herein. The instructions 1224 can also reside, completely or at least partially, within the main memory 1204, within static memory 1206, or within the processor 1202 during execution thereof by the machine 1200. In an example, one or any combination of the processor 1202, the main memory 1204, the static memory 1206, or the storage device 1216 can constitute machine readable media.

While the machine readable medium 1222 is illustrated as a single medium, the term "machine readable medium" can include a single medium or multiple media (e.g., a centralized or distributed database, and/or associated caches and servers) that configured to store the one or more instructions 1224. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1224 can further be transmitted or received over a communications network 1226 using a transmission medium via the network interface device 1220 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

The concept of an approach wherein the entropy measurement is used in conjunction with other time series measurements in the time and non-linear dynamical domains, may be implemented and utilized with the related processors, networks, computer systems, internet, and components and functions according to the schemes disclosed herein.

While example systems, methods, and so on, have been illustrated by describing examples, and while the examples have been described in considerable detail, it is not the intention to restrict or in any way limit the scope of the appended claims to such detail. It is, of course, not possible to describe every conceivable combination of components or methodologies for purposes of describing the systems, methods, and so on, described herein. Additional advantages and modifications will readily appear to those skilled in the art. Therefore, the invention is not limited to the specific details, and illustrative examples shown or described. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

The invention claimed is:

1. A system for detecting arrhythmia, the system comprising:
    a heart rhythm recording device including electrocardiogram (ECG) leads and a digital recording device;
    a classifier module comprising one or more processors, one or more computer-readable tangible storage devices, and program instructions stored on at least one of the one or more storage devices for execution by at least one of the one or more processors, the program instructions comprising:
        first program instructions to cause the one or more processors to obtain data consisting of a time series of the times between heartbeats from the heart rhythm recording device;
        second program instructions to cause the one or more processors to segment the time series into a plurality of segments;
        third program instructions to cause the one or more processors to calculate a plurality of parameters corresponding to each of the segments, the plurality of parameters consisting of heart rate dynamics of the time series of times between heartbeats, the heart rate dynamics including:
            an entropy measure that detects atrial fibrillation in interval time series data by counting how many template patterns repeat themselves;
            a quantitative measure of fractal-like scaling properties of interval time series data; and
            a local dynamics measure that determines how often individual templates in interval time series data match each other;
        fourth program instructions to cause the one or more processors to analyze via a plurality of multivariable algorithms for rhythm classification:
            the obtained data consisting of a time series of the times between heartbeats; and
            the plurality of parameters corresponding to each of the segments;
            the plurality of multivariable algorithms including at least one of: one or more logistic regression analysis algorithm or one or more K-nearest neighbor analysis algorithm;
            wherein analyzing for rhythm classification involves each algorithm of the plurality of multivariable algorithms determining a probability that one or more of sinus rhythm, premature atrial contractions, premature ventricular contractions, atrial fibrillation, or normal sinus rhythm is a predictor for rhythm classification; and
        fifth program instructions to cause the one or more processors to synthesize the results of the plurality of multivariable algorithms to formulate a single rhythm classification, the single rhythm classification including a highest predictor probability; and
    a processing device configured to receive the single rhythm classification and detect arrhythmia based on the single rhythm classification.

2. The system of claim 1, wherein the time series comprises 10 minutes in duration.

3. The system of claim 1, wherein the segments comprise 30 second intervals.

* * * * *